United States Patent [19]

Fleer

[11] Patent Number: 4,655,709

[45] Date of Patent: Apr. 7, 1987

[54] COUPLING DEVICE FOR DENTAL HANDPIECES

[75] Inventor: Ernst O. Fleer, Bensheim, Fed. Rep. of Germany

[73] Assignee: Siemens Aktiengesellschaft, Berlin and Munich, Fed. Rep. of Germany

[21] Appl. No.: 763,426

[22] Filed: Aug. 7, 1985

[30] Foreign Application Priority Data

Aug. 23, 1984 [DE] Fed. Rep. of Germany ....... 3431052

[51] Int. Cl.[4] ............................................. A61C 1/00
[52] U.S. Cl. ...................................... 433/29; 433/126
[58] Field of Search ................................. 433/126, 29

[56] References Cited

U.S. PATENT DOCUMENTS

| | | |
|---|---|---|
| 4,080,737 | 3/1978 | Fleer . |
| 4,278,428 | 7/1981 | Straihammer et al. . |
| 4,398,885 | 8/1983 | Loge et al. .............................. 433/29 |
| 4,561,845 | 12/1985 | Meller ..................................... 433/29 |
| 4,568,284 | 2/1986 | Stankiewicz ........................... 433/29 |

FOREIGN PATENT DOCUMENTS

| | | |
|---|---|---|
| 1068425 | 11/1959 | Fed. Rep. of Germany . |
| 2549177 | 5/1977 | Fed. Rep. of Germany . |
| 3108967 | 9/1982 | Fed. Rep. of Germany . |
| 1161157 | 8/1958 | France . |
| 2525462 | 10/1983 | France . |
| 2542189 | 9/1984 | France . |
| 2092450 | 8/1982 | United Kingdom . |

*Primary Examiner*—Robert Peshock

[57] ABSTRACT

A coupling device which enables coupling different types of dental handpieces or devices to a supply hose characterized by a pin-shaped coupling member which has a electrical lamp at a free end for supplying light to a waveguide in the dental device for discharge adjacent the head portion of the dental device and an arrangement of contacts for supplying electrical energy to contacts of a dental device to operate a lamp integrally formed in the dental device. Thus, the coupling device can interchangeably handle a dental device which has an integral lamp or a dental device which utilizes a light waveguide to conduct light from an outside light source to the operating area.

12 Claims, 7 Drawing Figures

COUPLING DEVICE FOR DENTAL HANDPIECES

BACKGROUND OF THE INVENTION

The present invention is directed to a coupling fixture or device operationally releasably connecting one of a plurality of differently designed dental devices or parts, such as the dental handpiece, which requires at least a coolant and light at a head part thereof, to a supply which contains the various fluids and electrical supply for a lamp. The coupling fixture or device includes a coupling member which in a coupling condition is received in an acceptance sleeve of the dental handpiece or device and which has coolant moving in channels and the coolant is transferred from the coupling member into channels of the acceptance sleeve which channels convey the fluid to the head part of the dental device or handpiece. In addition, the coupling member has internal electrical lines extending to a electrical lamp adjacent the front end of the coupling member so that light can be coupled from the coupling member to a light conductor in the dental device to be carried to the head thereof and also has an electrical arrangement on the coupling member to enable coupling electrical power to the dental device.

A coupling fixture or device where various different styles of handpieces such as turbine handpieces, spray handpieces, miniature motor handpieces and ultrasound handpieces can be optionally coupled to and uncoupled from a coupling part connected to a supply hose is disclosed in U.S. Pat. No. 4,080,737. In this coupling fixture, the coupling and uncoupling can be accomplished without the assistance of tools. In addition, to the agents such as air and water plus electrical power, light can also be transmitted at the coupling location. For the transmission of light, light supplying element in the form of an optical fiber or waveguide is disposed in the center of the coupling pin or tenon of the coupling member and a light receiving element, which may also be an optical fiber waveguide, is disposed in the end face of the handpiece. In the coupled condition of the handpiece and the coupling member, the ends of the light supplying optical fiber and the light receiving optical fiber are positioned opposite one another in a correspondingly optically coupled manner.

Another coupling fixture or device of a similar type is disclosed in U.S. Pat. No. 4,398,885. In this coupling device, the light supplying element is a lamp, which is operated through an electrical current. The lamp is mounted at the center of an end face of the pin-shaped coupling member in a correspondingly fashion lamp socket to which the electrical leads extend.

In addition to the above two types of arrangement for supplying light to a head of a dental device, another type is known where the lamp is disposed on the handpiece expediently in the proximity of the treatment head (See German AS No. 10 68 425). The voltage supply from the coupling member to the handpiece occurs through coacting concentrically disposed slip rings and wiper contacts which are arranged in the coupling member and handpiece.

The first two arrangements, where the lamp is positioned on either the coupling member or the hose side of the coupling member, have advantages that only one lamp need be provide given use of various handpieces in contrast to the last mentioned arrangement wherein a lamp must be provided for each handpiece. Another advantage of the first two arrangements are that no voltage carrying parts can be contacted with the removal of the handpiece and that the handpiece themselves need not be equipped with electrical contacts, lines or lamps. However, the arrangement of the lamp at the hose side of the coupling member is not appropriate for every case. An example of such a case is when as illustrated and disclosed in U.S. Pat. No. b 4,278,428, the handpiece itself is designed as a multipart handiece and only the head part provided with different gearing graduations or ratios is interchangeable. With such an arrangement, the parting location also required in a light relaying part of the handpiece would involve a not negligible light loss which due to the structure of the handpieces cannot usually be compensated by either a more powerful and hence larger lamp or by a light conductor having a larger cross-section.

SUMMARY OF THE INVENTION

The object of the present invention is to provide a coupling device which enables alternately receiving either dental devices, such as handpieces or parts that have integrated light conductors and externally disposed light generating elements, or dental devices, such as handpieces or parts that have integrated light generating elements. The coupling device enables easy switching from one to the other type of dental device as well as easy changing of the light supplying element when necessary.

To accomplish these objects, the present invention is directed to an improvement in a coupling device for operational releasable connection of a supply hose to one of a plurality of differently designed dental devices such as dental handpieces and parts each of which has a head part which requires a cooling agent which is received through a channel extending along the device and light at the head part, said coupling device including a coupling part containing a coupling member which is received in a acceptance sleeve of the handpiece, said acceptance sleeve and coupling member having coacting ports and channels for transferring the cooling agent to the channels in the dental device for flow to the head part, said coupling member at a free end having a lamp socket and electrical line extending from the lamp socket to the supply hose. The improvement comprising the coupling member containing contact arrangement which includes wiper contacts connected to the electrical leads, said contact arrangement being designed and disposed so that contacts of a lamp mounted in the socket and terminal contacts of a lamp disposed in the dental device are alternately connected to the contact arrangement so that the coupling member can be used both with dental devices having a lamp in the device with electrical leads leading to the acceptance sleeve and dental devices having light conductors extending to the acceptance sleeve.

The contact arrangement of the invention allows both light relaying handpieces i.e. handpieces having a through-light conductor as well as handpieces which themselves have a light generating element. Thus, the coupling member has both wiper contacts for transferring electricity from the coupling member to the dental device and a lamp adjacent the free end for optically connecting to a light conductor of the dental handpiece or device.

DESCRIPTION OF THE PREFERRED EMBODIMENTS

Figure 1:
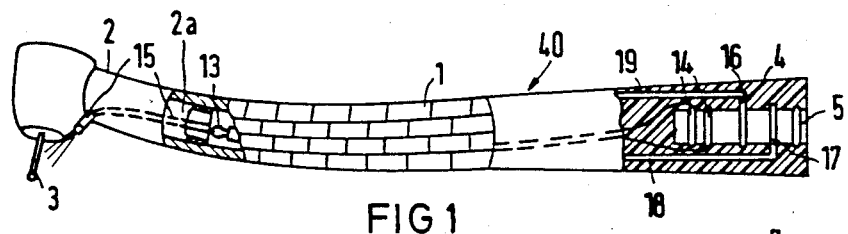
FIG. 1 is a side view with portion broken away for purposes of illustration of one embodiment of a turbine handpiece utilized with a coupling device of the present invention.
Figure 3:
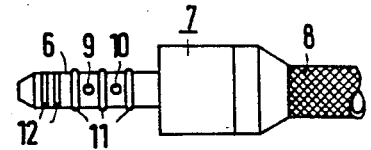
FIG. 3 is a side of a coupling device in accordance with the present invention.
Figure 2:
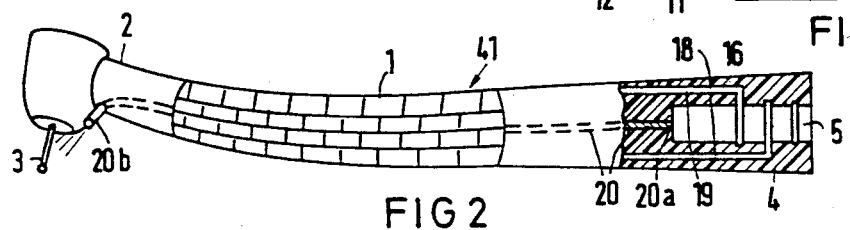
FIG. 2 is a side view with portions broken away of another embodiment of a handpiece utilized with the coupling device of the present invention.

The principles of the present invention are particularly useful in a coupling device 7 of FIG. 3 which is utilized with dental devices or handpieces 40 of FIG. 1 or 41 of FIG. 2. Both the handpiece 40 and 41 each have a elongated grip member 1 to which a head part 2 is connected. As illustrated in FIG. 1, the head part 2 has an end portion 2a which is telescopically received in the grip member 1 and can be uncoupled from the grip member 1 at this location. The part 2 also receives a drive arrangement such as an air turbine for rotating a tool 3 in a known fashion. The end of the grip member 1 facing away from the head part 2 forms a sleeve 4 having an acceptance bore or socket 5 into which a coupling member 6 in the form of a coupling pin of the coupling part 7 is telescopically received. A supply hose 8 in which supply lines for air and water as well as electrical leads are conducted is connected to the part 7. The supply lines for air and water extend to bores 9 and 10 which are provided in the circumference of the coupling member 6 and are sealed from one another by sealing rings 11. In addition, the coupling member has a contact arrangement formed by two contact or slip rings 12 with which as shall be explained later electrical energy can be transmitted to an incandescent light 13 disposed in a front end of the grip member 1 of the handpiece 40 approximate to the end portion 2a of the head part. This is done by a pair of cooperating contacts 14 which are provided in the bore 5 to engage the contacts 12 when the handpiece 40 is engaged on the coupling part 7. The contacts 14 are connected by electrical leads to the lamp 13. A light conductor 15, which has one end positioned opposite the lamp 13 and has its other end positioned to direct a light at the treatment location, acts to conduct light from the lamp 13 situated in the grip member 1 to the treatment location which is the position of the tool 3 in the head part 2.

In order to transmit fluid agents such as air and water through the handpiece 40, annular grooves 16 and 17 are positioned in the acceptance bore 5 to receive fluid from the respective ports 9 and 10 when the handpiece is connected to the part 7. Channels 18 extends from the groove 17 while channel 19 extends from the groove 16 and convey the various fluids up to the head part 2.

The handpiece 41 of FIG. 2 is identically constructed with respect to the transmission of the fluid such as air and water. In contrast to the handpiece 40 of FIG. 1, however, the handpiece 41 does not contain a light generating element or a lamp. The handpiece 41 does contain a light conductor 20 whose one end 20a lies in a region of the coupling location. The conductor 20 proceeds in the center at a suitable location inside of the handpiece 41 to an end 20b directed towards the treatment location indicated by the tool 3 in the head part 2.

Figure 4:
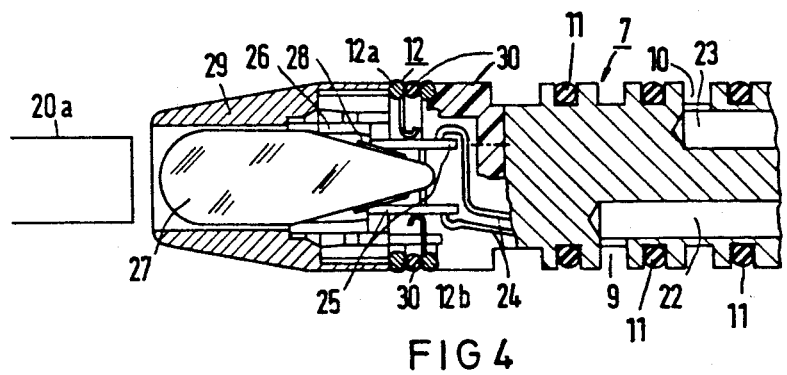
FIG. 4 is an enlarged longitudinal cross-sectional view of a coupling member of the device of FIG. 3.

A coupling member 6 is best illustrated in FIG. 4. The supply of air and water occurs in channel, such as 22 and 23 which proceed parallel to the axis of the pin-shaped coupling member 6 and the supplies are discharged at the circumference of the pin into the opening or ports 9 and 10. For the sake of greater clarity only two agents supply lines, for example, for propellant air and a cooling water have been illustrated in the exemplary embodiment. It should be noted, that additional lines for example for cooling air and/or return air can also be provided in the same fashion in a manner known per se.

The coupling member 6 has electrical leads 24, which conduct electrical energy to a first contact pair 25 which is originally disposed in an acceptance chamber or socket 26 for an incandescent lamp 27. This chamber 26 is opened at an end face of the member 6. The incandescent lamp 27 is provided with contacts 28 which engage the contact pair 25 after the lamp has been inserted into a mount or socket. As illustrated, a protective sleeve 29 for the lamp 27 can be screwed onto the member 6 and has an opened front end.

Figure 5:
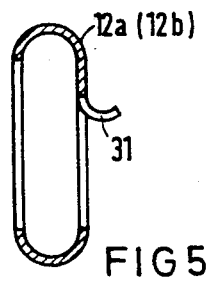
FIG. 5 is an enlarged cross-sectional view of a wiper contact of the coupling member of FIG. 4.

The pair of contacts 12 which comprise two annular contact springs 12a and 12b which are electrically insulated by insulators 30 from one another as well as from the usual metal coupling member 6 can be fashioned in accordance with a cross-sectional view illustrated in FIG. 5. Each of the springs 12a and 12b are provided with a resilient contact end 31 which respectfully engages one of the contact pairs 25 which are originally disposed in the cavity or socket 26. The provision of the second contact pair 12 in addition to the first contact pair, enables electricity to be conducted out of the member 6 and to its periphery. Thus, it is possible to attach both the handpiece 41 as shown in FIG. 2 which has a light receiving element to the coupling part 7 so that the end 20a of the light conductor is positioned opposite to the lamp 27 as best illustrated in FIG. 4. In addition is also possible to couple a handpiece 40 as shown in FIG. 1 which handpiece has a light generating element or lamp 13 in the handpiece without modifications having to be undertaken at the coupling part. The sleeve 4 of the grip member 1 as illustrated is constructed of an insulating material or at least the portion surrounding the coupling member 6 is of that type of material. This will cause an avoidance of a short when the handpiece 41 is attached to the coupling member 6.

In a modification of the invention, the coupling member 6 does not have the external contact rings 12. In order to provide for an electrical connection, the embodiment or modification utilizes an insert part 35, which is inserted into the lamp socket 26 in place of the lamp 27. The insert part 35 is provided with a contact pair 36 which are formed by annular contact bushings 36a and 36b and form interior socket portion. Each of the annular bushings 36a and 36b have a contact end 37 which extends through the part 35. The two contact ends 37 will engage the pair of fixed contacts 25 when the part 35 is plugged into the socket 26 in place of the lamp 27.

The dental handpiece or device which is utilized with this embodiment instead of being provided with contact pairs 14 in the interior of the bore 5 has a plug 38 which has stepped portions to form plug pins 38a and 38b which coact with the contact bushings 36a and 36b respectively. The plug 38 thus is connected in the fashion of a jack plug and is disposed centrally relative to the acceptance bore 5 at the location where the light conductor is situated in the handpiece 41 of FIG. 2.

The two disclosed solutions makes it possible given one and the same fitting of the coupling part to alternately provide both light relaying handpieces as shown in FIG. 2 as well as a light generating handpiece such as illustrated in FIG. 1. Thus, the changing over is possible at any time.

Even though two identical handpieces such as turbine handpieces have been shown in the exemplary embodiment, the proposal of the invention is conceivable not only for just drill drives but also on the contrary for other types of dental handpieces or devices such as ultrasound handpieces, electrosurgical handpieces, spray handpieces etc. Likewise, the proposal of the invention can be applied not only to dynamically balanced coupling parts whose purpose is to allow the attached handpiece to turn freely relative to the connector part. The proposal of the invention is just as applicable to pluggable handpieces or, respectively, handpiece parts.

Figure 7:
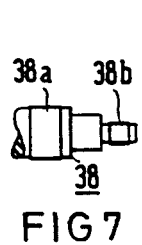
FIG. 7 is a partial side view of another member utilized with the contact arrangement of FIG. 6.
Figure 6:
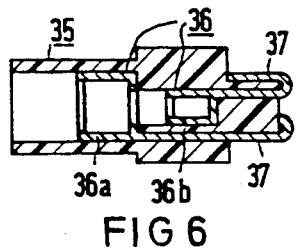
FIG. 6 is an enlarged cross-sectional view of a modification of a contact arrangement for the coupling member of FIG. 4.

Further, it is also possible to provide contact bushings or parts as shown in FIG. 6 to form the socket with the first contact pairs for a handpiece with a concentric plug according to FIG. 7 and also a socket for the lamp. The insert part which contains a second contact pair for the direct contacting of a lamp, is alternately attachable. In this case, the handpiece with the integrated lamp can be connected primarily and after insertion of an insert part with a corresponding lamp socket. A handpiece having a light receiving light conductor can be secondarily connected. The contact arrangement can also be advantageously designed for a direct connection of a lamp socket which receives its voltage via the slip rings.

Although various minor modifications may be suggested by those versed in the art, it should be understood that I wish to embody within the scope of the patent granted hereon all such modifications as reasonably and properly come within the scope of my contributions to the art.

I claim:

1. In a coupling device for the operationally releasably connection of a connecting part with a coupling member to one of a plurality of differently designed dental devices havng a head part which requires light and at least one fluid agent received in a channel in the dental device, said coupling member having a channel for each fluid agent, being engageable in an acceptance sleeve of the dental device and having a lamp at a free end of the coupling member, said lamp being engaged with a rigidly disposed pair of contacts connected to electrical leads extending through the coupling member and connecting part, and said coupling member and sleeve having coacting means for transferring fluid agent therebetween, the improvement comprising the coupling member containing a contact arrangement including said pair of contacts and two ring contacts, said contact arrangement being connected to the electrical leads, said contact arrangement being designed and disposed in the coupling member with the pair of contacts forming an electrical contact with the lamp being mounted in the coupling member and said ring contacts forming electrical contacts with terminal contacts provided in the acceptance sleeve of the dental device so that either a dental device having an integral lamp with terminal contacts or a dental device having a light conductor for conducting light from the lamp of the coupling member can be alternately coupled onto the member.

2. In a coupling device according to claim 8, wherein said two ring contacts of the insert part are annular contact bushings and wherein the dental device has cooperating contact elements in the form of a jack plug for being received in the insert part to form electric connection therebetween.

3. In a coupling device according to claim 1, wherein said pair of contacts are slip rings disposed in a lamp socket of the coupling member, and said two ring contacts are on an insert part which contain a terminal contacts for the lamp.

4. In a coupling device according to claim 3 wherein said insert part forms a lamp socket.

5. In a coupling device according to claim 1, wherein said coupling member is a cylindrically shaped pin member and said acceptance sleeve is a cylindrical bore.

6. In a coupling device according to claim 1, wherein said two ring contacts are disposed on a cylindrical outer surface of the coupling member, said arrangement including means for electrically connecting said two ring contacts to said pair of contacts and wherein in a coupled condition the two ring contacts electically engage correspondingly disposed cooperating contacts of the dental device.

7. In a coupling device according to claim 6, wherein said ring contacts are inserted in recesses on the cylindrical outer surface of the coupling member, and said means for electrically connecting being a terminal lug on each of the ring contacts extending into the coupling member to form a contact with the pair of contacts.

8. A coupling device according to claim 1, wherein said ring contacts are disposed on an insert part, said insert part being received in a lap socket of the coupling member in place of said lamp with extensions of the two ring contacts making electrical connections with the pair of contacts of the coupling member.

9. A coupling device for operationally releasably connection of a supply hose to one of a plurality of differently designed dental devices, said dental device having a head part requiring light, said coupling device including a coupling member connected to the supply hose and having a coupling pin telescopically received in a cylindrical acceptance bore of the dental device, said coupling pin at a free end being provided with a socket containing an electrically operated lamp, said socket having electrical leads extending through the coupling member and coupling device to the supply hose, the improvements comprising said coupling member containing a contact arrangement comprising ring contacts connected to the electrical leads so that the coupling member can either receive a dental device having an integrally formed lamp and electrical terminal contacts in the cylindrical acceptance bore or a dental device having a light waveguide positioned to receive light from said lamp in the coupling member.

10. In a coupling device according to claim 9 wherein said ring contacts are spaced along the pin of the coupling member for engagement by spaced contacts in the cylindrical acceptance bore of the dental device.

11. In a coupling device according to claim 9, wherein the head part of the dental device requires at least one fluid, said coupling part has a channel for each fluid required by the dental device, and said coupling member and coacting cylindrical acceptance bore have coacting ports and channels for each fluid to form a transfer therebetween.

12. In a coupling device for the operationally releasably connection of a supply hose to a plurality of differently designed dental devices each dental device having a head part requiring light, said coupling device including a coupling member which is received in an acceptance sleeve of the dental device, said coupling member adjacent a free end being provided with a electrical socket receiving a lamp, said socket having contacts connected to electrical leads extending through the coupling member to a supply hose, the improvement comprising an insert part for replacing the lamp, said insert part having a pair of spaced contact bushings having contact extensions engaging the contacts of said socket, said insert part receiving a jack plug having a pair of separate contacts, so that the coupling device can receive a dental device having a light conductor for receiving light from the lamp or by replacing the lamp with the insert part can receive a dental device having an integral lamp with leads extending to the jack plug to supply power to the integral lamp.

* * * * *